(12) United States Patent
Lim et al.

(10) Patent No.: US 9,920,092 B1
(45) Date of Patent: *Mar. 20, 2018

(54) COMPOSITION HAVING ANTI-OXIDANT, ANTI-AGING, AND AUTOPHAGY ACTIVITIES AND USES THEREOF

(71) Applicant: Incospharm Corporation, Yuseong-gu, Daejeon (KR)

(72) Inventors: Chae Jin Lim, Daejeon (KR); Myung Ho Kor, Daejeon (KR); Seok Jeong Yoon, Daejeon (KR); Jin A Kim, Daejeon (KR); Heung Jae Kim, Daejeon (KR); Kee Don Park, Daejeon (KR)

(73) Assignee: Incospharm Corporation, Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/618,875

(22) Filed: Jun. 9, 2017

(51) Int. Cl.
  *A61K 8/64* (2006.01)
  *A61K 38/05* (2006.01)
  *C07K 5/068* (2006.01)
  *A23L 33/10* (2016.01)

(52) U.S. Cl.
  CPC .......... *C07K 5/06086* (2013.01); *A23L 33/10* (2016.08); *A23V 2002/00* (2013.01)

(58) Field of Classification Search
  CPC ...... C07K 5/06104; A61K 8/64; A61K 38/05; A61Q 19/007; A61Q 19/00
  See application file for complete search history.

(56) References Cited

U.S. PATENT DOCUMENTS 9,359,401 B2 * 6/2016 Park ..................... C07K 14/001

FOREIGN PATENT DOCUMENTS

KR  10-1705338 B1  2/2017

OTHER PUBLICATIONS

Wickipedia, Wickipedia, Ethylenediaminetetraacetic acid, 2017, recovered from internet on Jul. 19, 2017 at https://en.wikipedia.org/wiki/ Ethylenediaminetetraacetic_acid, pp. 1-9.*
Nixon, Nature Medicine, The role of autophagy in neurodegenerative disease, 2013, 19, pp. 983-997.*
Rubinsztein et al, Cell, Autophagy and Aging, 146, Sep. 2, 2011, pp. 882-896.*
Yu Gan et al., "Transgenic Overexpression of Peroxiredoxin-2 Attenuates Ischemic Neuronal Injury Via Suppression of a Redox-Sensitive Pro-Death Signaling Pathway," Antioxidants & Redox Signaling, 2012, pp. 719-732, vol. 17, No. 5.
Shih-Ya Hung et al., "Autophagy protects neuron from Aβ-induced cytotoxicity," Autophagy, May 16, 2009, pp. 502-510, vol. 5, No. 4.
Maria Xilouri et al., "Boosting chaperone-mediated autophagy in vivo mitigates α-synuclein-induced neurodegeneration," BRAIN—A Journal of Neurology, 2013, pp. 2130-2146, vol. 136.
Fang Zhao et al., "The protective effect of peroxiredoxin II on oxidative stress induced apoptosis in pancreatic β-cells," Cell & Bioscience, 2012, pp. 1-9, vol. 2, No. 22.
Shouji Matsushima et al., "Overexpression of Mitochondrial Peroxiredoxin-3 Prevents Left Ventricular Remodeling and Failure After Myocardial Infarction in Mice," Circulation, Apr. 3, 2006, pp. 1779-1786, vol. 113.
Jinyoung Kim et al., "Amyloidogenic peptide oligomer accumulation in autophagy-deficient β cells induces diabetes," The Journal of Clinical Investigation, Aug. 2014, pp. 3311-3324, vol. 124, No. 8.
Lin Qi et al., "The Role of Chaperone-Mediated Autophagy in Huntingtin Degradation," PLOS one, Oct. 2012, pp. 1-10, vol. 7, No. 10.

* cited by examiner

Primary Examiner — Paul A Zucker
(74) Attorney, Agent, or Firm — Sughrue Mion, PLLC

(57) ABSTRACT

Provided are a composition having anti-oxidant, anti-aging, and autophagy activities to thereby be useful for preventing, alleviating, or treating age-related metabolic diseases including neurodegenerative diseases or type 2 diabetes, and uses thereof.

5 Claims, 11 Drawing Sheets

COMPOSITION HAVING ANTI-OXIDANT, ANTI-AGING, AND AUTOPHAGY ACTIVITIES AND USES THEREOF

TECHNICAL FIELD

The following disclosure relates to a composition having anti-oxidant, anti-aging, and autophagy activities to thereby be useful for preventing, alleviating, or treating aging-related metabolic diseases including neurodegenerative diseases and type 2 diabetes, and uses thereof.

BACKGROUND

Due to an aging phenomenon continuing around the world, Korea is predicted to become an aged society where the percentage of people over 65 years old is 14% or more of the total population by 2018. Since an increase in aging population means an increase in a percentage of population having chronic diseases or deteriorated biological functions, anti-aging industries, for example, a pharmaceutical industry, a functional food industry, a cosmetic industry, and the like, for satisfying the needs for healthy life and improving health of old-aged people are expected to be developed.

Further, in middle-aged people, there is growing demand for improving various biological indices associated with aging before they got too old, and there is growing desire to live in a healthier and more youthful state. Further, since in terms of gender distribution, the proportion of women participating in economical and social activities has gradually increased, there is a large need to develop anti-aging materials and products for women, and among them, a demand for a product of which scientific efficacy is clearly proven has gradually increased.

In order to satisfy the demand for the anti-aging product as described above, there is a need to understand main features in aged tissue and cells and to seek a method for alleviating the aging. As the main feature in cells configuring aged tissue or organs, there is a decrease in intracellular anti-oxidant activity for protecting cells from oxidative stress and/or a rapid decrease in autophagy activity. As the intracellular anti-oxidant activity and/or the autophagy activity is decreased, cell viability and activity are rapidly decreased, such that morphological aspects of the aging appear, thereby leading to cell aging and metabolic diseases such as neurodegenerative diseases, type 2 diabetes, or the like.

Autophagy means a mechanism to regenerate energy and remove damaged materials by decomposing aged or damaged materials and organelles in cells when an energy source in the cells is exhausted or stress factors in cells are excessively generated, and enables maintenance of normal cells. Recently, in various studies, it was reported that as the aging has proceeded or been accelerated, an autophagy activity in cells has rapidly decreased. On the contrary, in the case of suppressing the autophagy activity, aged mitochondria, misfolded proteins, or the like, are excessively accumulated in cells, such that free radicals and oxidative stress in the cells are increased, thereby resulting in increasing apoptosis and promoting aging.

Further, in mitochondria, while an energy generation process is performed, reactive oxygen species are formed as by-products, and lipid peroxide, a lipid peroxy radical, peroxynitrite, or the like, is formed by external stress such as ultraviolet light, drugs, materials taken into the body, and stimulation of environmental contamination factors, or the like, thereby applying a wide oxidative stress. These oxidative stress products are significantly unstable and have high reactivity with surrounding materials to significantly strongly bind to proteins, lipids, deoxyribonucleic acid (DNA), or the like, in cells, and cause various denaturation, which results in causing fetal problems.

An example of a material capable of increasing the intracellular anti-oxidant activity may include anti-oxidant materials such as vitamins, glutathione, coenzyme Q10, and the like, or anti-oxidant proteins such as catalase, superoxide dismutase, glutathione-dependent peroxidase, peroxiredoxin, and the like. However, these anti-oxidant materials according to the related art have problems in that they may exhibit an excellent reactive oxygen scavenging activity in-vitro and in the blood, but these anti-oxidant materials may rather increase formation of reactive oxygen in cells depending on the concentration. Further, proteins, lipid, mitochondria, and the like, denatured by oxidative stress may be rapidly removed by activating autophagy, a recycling mechanism to decompose aged materials and organelles in cells, such that an environment in which cells may live in a healthier state may be provided.

In order to remove this oxidative stress generated in cells and recover health of an individual, tissue, and cells, the anti-oxidant activity and autophagy activation in the cells are significantly important. Therefore, in order to basically solve problems of the anti-oxidant materials according to the related art and provide an excellent anti-aging effect, there is a need to develop a material having an excellent effect of inducing autophagy activation while increasing expression of anti-oxidant proteins in cells to increase the anti-oxidant activity.

RELATED ART DOCUMENT

Non-Patent Document

Gan et al., Anti-oxidants & Redox Signaling, 2012, 17, 5, 719-732
Matsushima et al., Circulation, 2006, 113, 1779-1786
Zhao et al., Cell & Bioscience, 2012, 2, 22
Hung et al., Autophagy, 2009, 5, 4, 502-510
Qi et al., PLOS one, 2012, 7, 10, e46834
Xilouri et al., Brain, 2013, 136, 2130-2146
Kim et al., The Journal of Clinical Investigation, 2014, 124, 8, 3311-3324

SUMMARY

Therefore, the present inventors tried to develop a material capable of activating anti-oxidant and autophagy mechanism, and as a result, the present inventors found that a compound represented by Structural Formula 1 in the present invention may have an effect of increasing expression of autophagy-related proteins to activate autophagy while increasing expression various anti-oxidant proteins in cells, and finally protect cells from oxidative stress, thereby completing the present invention.

An embodiment of the present invention is directed to providing a compound represented by Structural Formula 1 of the present invention, or a pharmaceutically acceptable salt thereof.

Another embodiment of the present invention is directed to providing an anti-oxidant and/or anti-aging composition containing a compound represented by Structural Formula 1 of the present invention, or a pharmaceutically acceptable salt thereof.

Another embodiment of the present invention is directed to providing a pharmaceutical composition for preventing and/or treating a cell aging-related disease selected from the group consisting of neurodegenerative diseases and type 2 diabetes, containing a compound represented by Structural Formula 1 of the present invention, or a pharmaceutically acceptable salt thereof.

Another embodiment of the present invention is directed to providing a food composition for preventing and/or alleviating a cell aging-related disease selected from the group consisting of neurodegenerative diseases and type 2 diabetes, containing a compound represented by Structural Formula 1 of the present invention, or a sitologically acceptable salt thereof.

Another embodiment of the present invention is directed to providing an anti-oxidant and/or anti-aging method including administering step an effective dose of a compound represented by Structural Formula 1 of the present invention, or a pharmaceutically acceptable salt thereof to an individual.

Another embodiment of the present invention is directed to providing a method of treating a cell aging-related disease selected from the group consisting of neurodegenerative diseases and type 2 diabetes, including administering step an effective dose of a compound represented by Structural Formula 1 of the present invention, or a pharmaceutically acceptable salt thereof to an individual.

In tissue and cells of young people, an intracellular anti-oxidant activity is high and autophagy is activated, but as an aging process proceeds, since expression amounts of anti-oxidant proteins and autophagy-related proteins in cells are rapidly decreased, it is impossible to protect individual cells from oxidative stress. Therefore, it is possible to suppress the aging of each cell, tissue, and individual and treat various diseases caused by the aging by protecting each cell from the oxidative stress and activating autophagy.

It was confirmed that a compound provided in the present invention increases expression of anti-oxidant-related proteins such as a peroxiredoxin2 (Prx2) monomer, Prx3, heat shock protein70 (HSP70) based glucose regulated protein75 (Grp75), HSP90B1, epoxide dehydrogenase2 (EPHX2), stanniocalcin2, and the like (FIG. 5) and expression of autophagy and detoxification-related proteins such as binding immunoglobulin protein (BiP), forkhead box protein O1 (FoxO1), and sirtuin5 (FIG. 6). Further, it was confirmed that the compound provided in the present invention increases an anti-oxidant activity in-vitro and in cells (FIGS. 3 and 4), has an effect of activating autophagy in cells (FIGS. 7 to 9), and finally has an effect of protecting cells from oxidative stress (FIGS. 10 and 11).

Among various kinds of anti-oxidant proteins, peroxiredoxins are known as core proteins protecting cells and organelles in cells from oxidative stress, and an increase in expression of these proteins is expressed as an immediate cell protection effect. According to the related art, there was no material reported to increase expression of the peroxiredoxin protein, and only a case in which an effect was proven by inserting a gene into a cell in a form of a plasmid to form a gene-modified cell and individual to over-express a target protein was reported. Representatively, it was reported that in the case of over-expressing peroxiredoxin2, an effect of protecting nerve tissue from ischemic neuronal injury may be obtained (Gan et al., Anti-oxidants & Redox Signaling, 2012, 17, 5, 719-932) and it was reported that in the case of over-expressing peroxiredoxin3, an effect of protecting tissue from heart failure caused by myocardial infarction may be obtained (Matsushima et al., Circulation, 2006, 113, 1779-1786). Further, it was reported that in the case of over-expressing peroxiredoxin2 in pancreatic beta cells, an effect of protecting the beta cells from apoptosis generated due to oxidative stress was exhibited (Zhao et al., Cell & Bioscience, 2012, 2, 22). Therefore, it was confirmed through the above-mentioned reports that in the case of promoting expression of peroxiredoxin in cells, it is possible to treat various diseases caused by aging, for example, nervous system diseases, myocardial diseases, diabetes, or the like.

Further, activation of autophagy may improve viability of aged cells by removing harmful proteins and organelles in cells, and is closely associated with an increase in life expectancy of each individual.

According to the prior reports, activation of autophagy may minimize damage of nerve cells by decreasing accumulation of beta-amyloid, which is a main cause of Alzheimer's disease, to protect cells from cytotoxicity by beta-amyloid (Hung et al., Autophagy, 2009, 5, 4, 502-510). In addition, activation of autophagy may decompose and remove mutant huntingtin, which is a main cause of Huntington's disease, thereby making it possible to suggest a possibility of alleviating and treating symptoms of Huntington's disease (Qi et al., PLOS one, 2012, 7, 10, e46834). Further, activation of autophagy may suppress accumulation of alpha-synuclein, which is a main cause of Parkinson's disease, to provide an effect of alleviating neuronal degeneration by alpha-synuclein (Xilouri et al., Brain, 2013, 136, 2130-2146), and may prevent occurrence of type 2 diabetes by removing a toxic oligomer form of human pancreatic amyloid polypeptide, which destructs pancreatic beta cells to cause type 2 diabetes, thereby making it possible to suggest a possibility of alleviating and treating symptoms of type 2 diabetes caused by the toxic oligomer form of human pancreatic amyloid polypeptide (Kim et al., The Journal of Clinical Investigation, 2014, 124, 8, 3311-3324). Therefore, through the above-mentioned reports, it may be confirmed that in the case of activating autophagy in cells, it is possible to treat various diseases caused by the aging, for example, neurodegenerative diseases (Alzheimer's disease, Huntington's disease, Parkinson's disease, and the like), type 2 diabetes, or the like.

As a result, since the compound provided in the present invention has an effect of increasing expression of the anti-oxidant proteins such as peroxiredoxin and activating autophagy, the compound may be used to prevent, alleviate, or treat neurodegenerative diseases (Alzheimer's disease, Huntington's disease, Parkinson's disease, and the like), or type 2 diabetes.

Therefore, in one general aspect, there is provided a compound having an excellent anti-oxidant and autophagy activities, or a pharmaceutically acceptable salt thereof.

In more detail, the present invention provides a compound represented by the following Structural Formula 1 or a pharmaceutically acceptable salt thereof.

[Structural Formula 1]

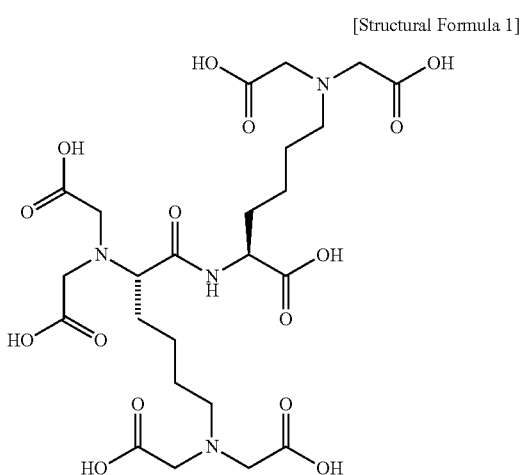 [SMILES: O=C(O)CN(CCCC[C@H](NC(=O)[C@H](CCCCN(CC(=O)O)CC(=O)O)N(CC(=O)O)CC(=O)O)C(=O)O)CC(=O)O]

The compound is named 2-[2,6-bis-(bis-carboxymethyl-amino)-hexanoyl-amino]-6-(bis-carboxymethyl-amino)-hexanoic acid.

In another general aspect, there is provided an anti-oxidant and/or anti-aging composition containing a compound represented by Structural Formula 1, or a pharmaceutically acceptable salt thereof.

In another general aspect, there is provided a pharmaceutical composition for preventing and/or treating a cell aging-related disease selected from the group consisting of neurodegenerative diseases and type 2 diabetes, containing a compound represented by Structural Formula 1 or a pharmaceutically acceptable salt thereof.

In another general aspect, there is provided a food composition for preventing and/or alleviating a cell aging-related disease selected from the group consisting of neurodegenerative diseases and type 2 diabetes, containing a compound represented by Structural Formula 1 or a sitologically acceptable salt thereof.

In another general aspect, there is provided an anti-oxidant and/or anti-aging method including administering step an effective dose of a compound represented by Structural Formula 1 or a pharmaceutically acceptable salt thereof to an individual.

In another general aspect, there is provided a method of treating a cell aging-related disease selected from the group consisting of neurodegenerative diseases and type 2 diabetes, including administering step an effective dose of a compound represented by Structural Formula 1 or a pharmaceutically acceptable salt thereof to an individual.

The compound according to the present invention or the pharmaceutically acceptable salt thereof may be prepared using a general method known in the art.

In the present specification, the term 'pharmaceutically acceptable salt' includes salts derived from pharmaceutically acceptable inorganic acids, organic acids, or bases. A suitable example of the acid includes hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, trifluoroacetic acid, citric acid, methanesulfonic acid, formic acid, benzoic acid, malonic acid, naphthalane-2-sulfonic acid, benzenesulfonic acid, or the like. A salt derived from a suitable base may contain an alkali metal such as sodium, or the like, an alkali earth metal such as magnesium, or the like, ammonium, etc.

In the present specification, the neurodegenerative diseases may include Alzheimer's disease, Huntington's disease, Parkinson's disease, or the like.

The composition according to the present invention may be provided in various forms such as a pharmaceutical composition, a food composition, a cosmetic composition, or the like, depending on the purpose.

In the case in which the composition according to the present invention is provided as the cosmetic composition, the composition may be used for skin external application, or be transdermally or subcutaneously administered depending on an administration route as an anti-oxidant or anti-aging functional cosmetic composition. It is preferable that the composition may be a composition capable of being used for skin external application or being transdermally administered. More preferably, the composition may be a composition capable of being used for skin external application.

The cosmetic composition, which means a composition capable of being transdermally applied to the skin, the scalp, or the hair, and used to prepare all cosmetic products including basic cosmetics, makeup cosmetics, body products, shaving products, hair products, and the like, may be formulated into formulations such as plasters, sprays, suspensions, emulsions, creams, gels, foams, or the like, but the formulation of the cosmetic composition is not particularly limited.

A content of the compound contained the cosmetic composition may be suitably adjusted depending on a use, an application formulation, use purpose, and a desired effect of the composition. In consideration of an effect in comparison with the content, the content of the compound may be 0.0001 to 1 wt %, preferably 0.001 to 0.5 wt %, and most preferably, 0.03 to 0.1 wt % based on a weight of an entire cosmetic composition. When the content of the compound according to present invention is below the above-mentioned range, it is impossible to obtain the effect of substantially increasing expression of the anti-oxidant proteins and activating autophagy, and when the content exceeds the above-mentioned range, stability of the formulation may be deteriorated due to high hygroscopicity of the present material. Therefore, it is preferable that the content of the compound is within the above-mentioned range.

The cosmetic composition may additionally contain all kinds of ingredients capable of being generally used for production or preparation, for example, a perfume, a pigment, a disinfectant, an anti-oxidant, a preservative, a moisturizer, a thickener, an excipient, a diluent, inorganic salts, a synthetic polymer material, and the like, in addition to the compound as an active ingredient, and the kinds and contents thereof may be suitably adjusted depending on uses and purposes of a final product.

Further, the cosmetic composition may contain a solvent generally contained in an application formulation thereof. For example, the cosmetic composition may contain one or more selected from ethanol, glycerin, butylene glycol, propylene glycol, polyethylene glycol, 1,2,4-butanetriol, sorbitol ester, 1,2,6-hexanetriol, benzylalcohol, isopropanol, butanediol, diethylene glycol monoethylether, dimethyl isosorbide, N-methyl-2-pyrrolidone, propylene carbonate, glycereth-26, methyl gluceth-20, isocetyl myristate, isocetyl octanoate, octyldodecyl myristate, octyldodecanol, isostearyl isostearate, cetyl octanoate, neopentyl glycol dicaprate, and the like. In the case of preparing the composition according to the present invention using the solvent as described above, solubility of the compound in the solvent is slightly changed depending on the kind of compound or a mixing ratio of the solvent. However, those skilled in the art to which the present invention pertains may suitably select and apply the kind of solvent and a use amount thereof depending on characteristics of a product.

In addition, the cosmetic composition may contain various materials for enhancing transdermal administration at the time of transdermally administering the cosmetic composition. For example, the cosmetic composition may contain a laurocapram derivative, oleic acid, ester derivatives of monooleate derivative, adapalene, tretinoin, retinaldehyde, tazarotene, salicylic acid, azelaic acid, glycolic acid, ethoxy diglycol, Tween 80, lecithin organogel, or the like. Further, in order to impart additional functions, the cosmetic composition according to the present invention may further contain other ingredients such as a cosurfactant, a surfactant, an anti-dandruff agent, a callus softener, a blood flow stimulant, a cell activator, a refreshing agent, a moisturizer, an anti-oxidant, a pH adjuster, purified water, or the like, as long as the effect of increasing expression of anti-oxidant proteins and activating autophagy by the composition according to the present invention is not inhibited. Depending on the application formulation, the cosmetic composition may contain suitable additives such as a perfume, a pigment, a preservative, an excipient, or the like.

In the case in which the composition according to the present invention is provided as a pharmaceutical composition, the composition may exhibit an effect of preventing or treating various aging phenomena caused by the aging of cells and aging-related diseases by increasing expression of the anti-oxidant proteins and activating autophagy.

For example, the pharmaceutical composition provided in the present invention may have an effect of preventing or treating Alzheimer's disease, Huntington's disease, Parkinson's disease, and type 2 diabetes caused by mutant alpha-amyloid, huntingtin, alpha-synuclein, and the toxic oligomer form of human pancreatic amyloid polypeptide, respectively, by increasing expression of the anti-oxidant proteins and activating autophagy.

The pharmaceutical composition according to the present invention may be mainly orally, intravenously, intraperitoneally, intramuscularly, and subcutaneously administered. Further, the pharmaceutical composition may be formulated into oral formulations such as powders, granules, tablets, capsules, suspensions, emulsions, syrups, aerosols, and the like, external preparations, suppositories, sterile injection solutions, or the like, to thereby be used, but the formation of the pharmaceutical composition is not particularly limited.

The composition according to the present invention may additionally contain pharmaceutically acceptable additives generally used to prepare a pharmaceutical composition. The term "pharmaceutically acceptable additive" means a carrier or a diluent that does not excessively stimulate living organism nor inhibit biological activity and properties of an administered compound. In addition, the additive may improve preparation, compactibility, appearance, and taste of a medicines. For example, if necessary, a stabilizer, a surfactant, a lubricant, a solubilizer, a buffer, a sweetener, a base, an adsorbent, a taste corrective, a binder, a suspending agent, a hardener, an anti-oxidant, a brightener, a fragrance, a flavoring agent, a pigment, a coating agent, a wetting agent, a humectant, a filler, a defoaming agent, a refreshing agent, a chewable agent, an antistatic agent, a coloring agent, a sugar coating agent, an isotonic agent, a softener, an emulsifier, a tackifier, a thickener, a foaming agent, a pH adjusting agent, an excipient, a dispersant, a disintegrant, a waterproof agent, an antiseptic agent, a preservative, a solubilizing agent, a solvent, a flowing agent, or the like, may be added.

As an example, formulations for oral administration include tablets, pills, powders, granules, capsules, and the like, and these formulations may contain at least one excipient and/or lubricant, etc. Liquid formulations for oral administration include suspensions, solutions, emulsions, syrups, and the like, and these liquid formulations may contain various excipients such as a wetting agent, a sweetener, a sweetener, an aromatic piece, a preservative, or the like, as well as water and liquid paraffin that are generally used simple diluents. In addition, formulations for parenteral administration include sterile aqueous solutions, non-aqueous solvents, suspensions, emulsions, freeze-dried formulations, suppositories, and the like.

A content of the compound contained in the pharmaceutical composition may be suitably adjusted depending on uses, an application formulation, use purpose, and a desired effect of the pharmaceutical composition. In consideration of an effect in comparison with the content, the content of the compound may be, for example, 0.0001 to wt %, preferably 0.001 to 5 wt %, and most preferably, 0.03 to 1 wt % based on a weight of an entire composition. When the content of the compound is below the above-mentioned range, it is impossible to obtain the effect of substantially increasing expression of the anti-oxidant proteins and activating autophagy, and when the content exceeds the above-mentioned range, stability of the formulation may be deteriorated due to high hygroscopicity of the present material. Therefore, it is preferable that the content of the compound is within the above-mentioned range.

A preferable administration dose of the pharmaceutical composition may be changed depending on a state and weight of a patient, a degree of disease, a formulation, and an administration route and duration, but be appropriately selected by those skilled in the art. In order to obtain a more preferable effect, a daily administration dose of the composition according to the present invention may be preferably 0.1 mg/kg to 100 mg/kg based on the active ingredient, but is not limited thereto. One dose may be administered once a day, or divided into several doses and then administered several times. A pharmaceutical administration form of the composition according to the present invention may also be a form of a pharmaceutically acceptable salt of the active ingredient. Further, the composition may be used alone, or a suitable set as well as a combination of the compound with another pharmaceutically active compound may also be used.

In the case in which the composition according to the present invention is provided as a food composition, the food composition may contain an acceptable food auxiliary additive, and further contain a suitable carrier, excipient, and diluent which are generally used to prepare functional food.

In the present specification, the term 'food' means a natural substance or processed goods containing one kind or more of nutrients, preferably in a state in which it is subjected to a processing process to some extent so as to be directly edible. As a general meaning, the term "food" includes various foodstuffs, health functional food, drinks, food additives, and drink additives. Examples of the food include various foodstuffs, drinks, gums, teas, vitamin complex, functional food, and the like. Further, in the present invention, the food includes special nutritious food (for example, milk formulas, baby and toddler meal, and the like), meat products, fish products, tofu, jellies, noodles, (for example, ramen, dried noodles, and the like), health supplement food, seasoned food (for example, soy sauce, soybean paste, hot pepper paste, mixed sauce, and the like), sauces, confectionery (for example, snacks), dairy products (for example, fermented milk, cheese, and the like), other processed foods, kimchi, salted food (various kinds of kimchi, jangachi (Korean pickle), and the like), drinks (for example, fruit drinks, vegetable drinks, soybean milk, fermented drinks, ice cream, and the like), natural seasoning (for example, ramen seasoning, or the like), vitamin complex, alcoholic drink, alcohols, and other health supplement foods, but is not limited thereto. The health functional food, the drink, the food additive, or the drink additive may be prepared by a general preparation method.

Further, an amount of the compound contained in the food may be 0.00001 wt % to 50 wt % based on a total weight of the food, and in the case in which the food is the drink, the compound may be contained in a range of 0.001 g to 50 g, preferably 0.01 g to 10 g based on a total volume (100 ml) of the food, but the content of the compound is not limited thereto.

DETAILED DESCRIPTION OF EMBODIMENTS

Figure 1:
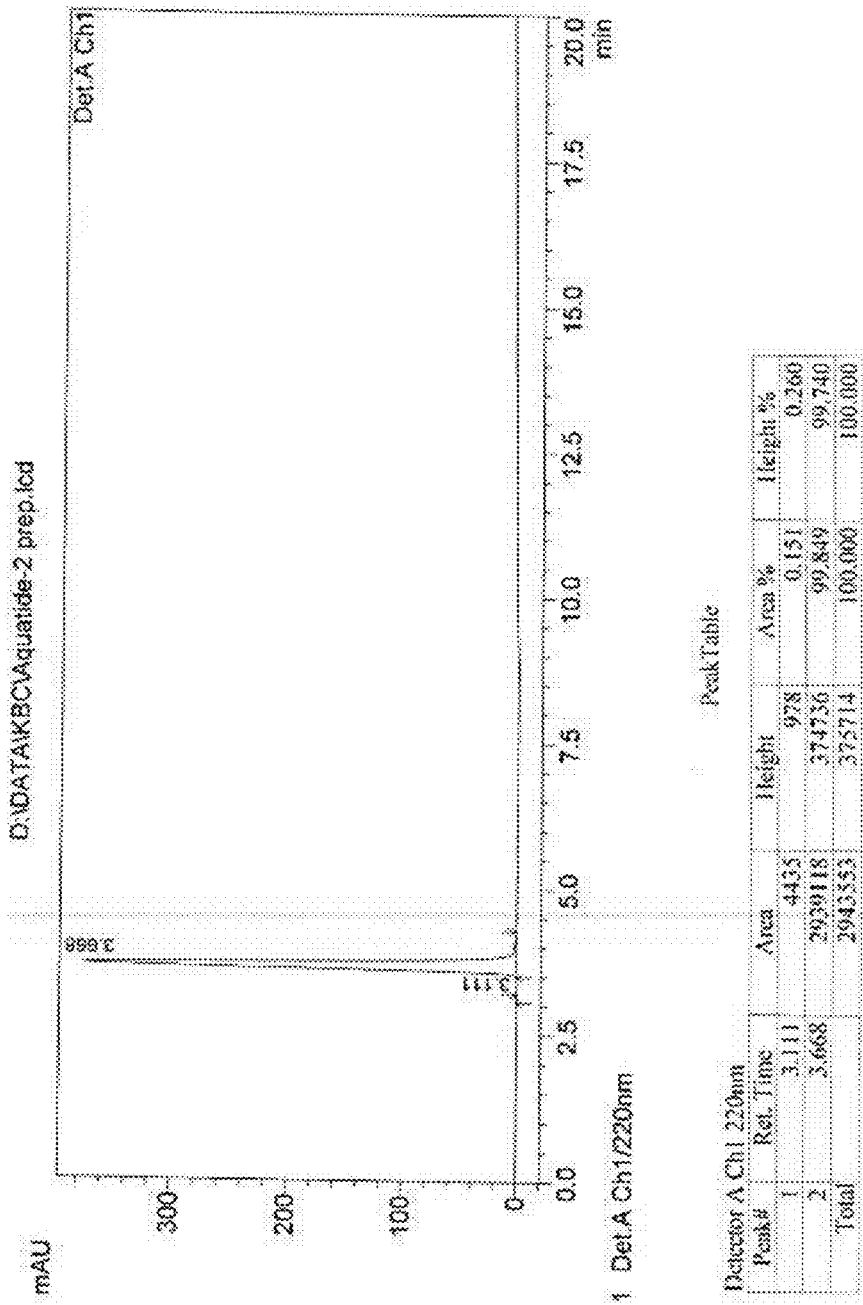
FIG. 1 illustrates a result obtained by performing high performance liquid chromatography (HPLC) assay on a compound represented by Structural Formula 1.

Hereinafter, the present invention will be described in detail by Examples. However, the following Examples are to illustrate the present invention, and the scope of the present invention is not limited to the following Examples.

Example 1. Synthesis of Compound Represented by Structural Formula 1

A compound represented by Structural Formula 1 according to the present invention was synthesized through a H-Lys-Lys-OH backbone synthesis process (first process), an alkylation reaction process (second process), a hydrolysis reaction process (third process), and a protection group removal reaction process (final process). A detailed description thereof is as follows.

Example 1-1. Synthesis of H-Lys-Lys-OH (Compound 1c)

1. Synthesis of Boc-Lys(Boc)-Lys(Boc)-OMe (Compound 1a)

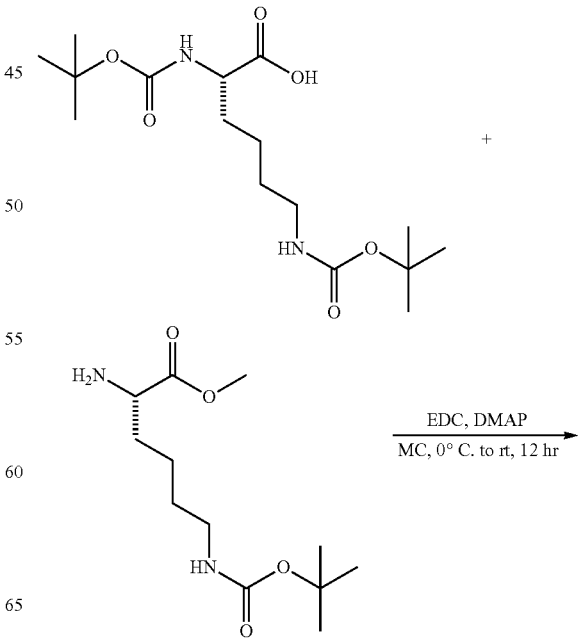

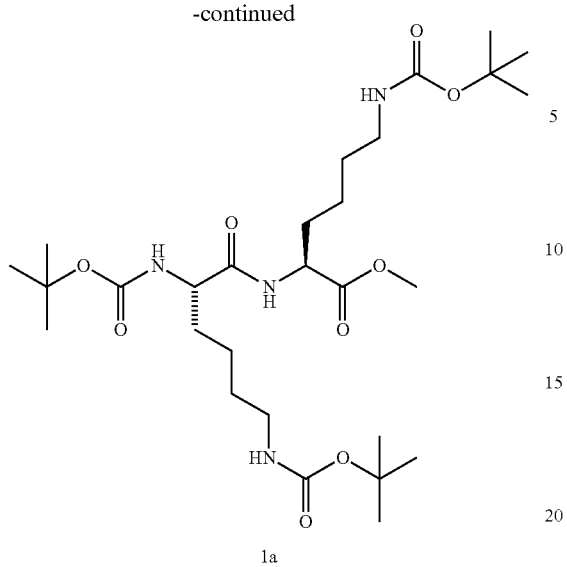

1a

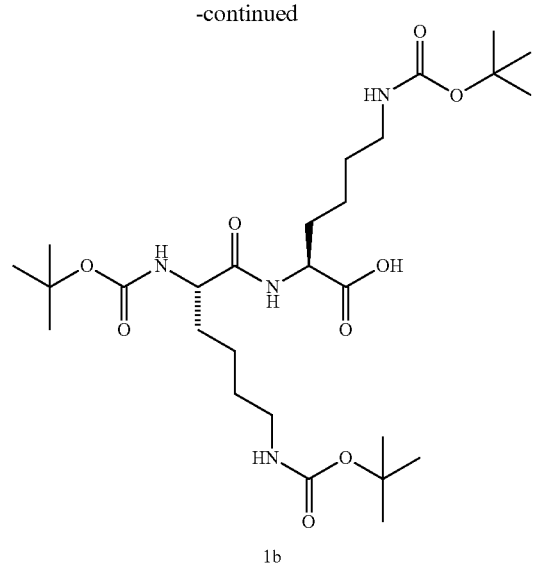

1b 50 g of Boc-Lys(Boc)-OH (1 equivalent: 144.35 mmol) and 45.09 g of H-Lys(Boc)-OMe (1.2 equivalents) were put into a 2 L round flask and dissolved in 500 ml of dichloromethane (MC). 1.76 g of N,N-dimethylaminopyridine (DMAP, 0.1 equivalents) was added thereto and a temperature of a reactant was lowered to 0° C. using an ice bath. 36 g of N-(3-Dimethylaminopropyl)-N'-ethylcarbodiimide hydrochloride (EDC, 1.3 equivalents) was dissolved in 300 ml of MC and slowly added thereto. When addition of EDC was terminated, the temperature of the reactant was slowly raised to room temperature, and a reaction was carried out for 12 hours. The reaction was confirmed by thin layer chromatography (TLC, hexane:ethyl acetate=1:1, Rf=0.4). The solvent was removed using a concentrator. After adding 500 ml of ethyl acetate (EA) and 500 ml of an aqueous 1N HCl solution, an EA layer was extracted using a separatory funnel. After 500 ml of an aqueous 5% NaHCO$_3$ solution was added thereto, an EA layer was extracted using a separatory funnel. After 20 ml of a saturated aqueous NaCl solution was added thereto, an EA layer was extracted using a separatory funnel. After adding Na$_2$SO$_4$ thereto to remove water, the resultant was concentrated. 76.4 g of Compound 1a was obtained (yield: 90%).

2. Synthesis of Boc-Lys(Boc)-Lys(Boc)-OH (Compound 1b)

50 g of Compound 1a (84.98 mmol, 1 equivalent) was put into a 2 L round flask, and dissolved by adding 500 ml of methanol thereto. 170 ml (1 equivalent) of an aqueous 1N NaOH solution was added thereto, and a reaction was carried out at room temperature for 12 hours. The reaction was confirmed by thin layer chromatography (TLC, MC:MeOH=10:1, Rf=0.4). Methanol was removed using a concentrator. After adding 500 ml of water thereto to dissolve the resultant, a pH of an aqueous solution was adjusted to 5 by adding sulfuric acid thereto. After adding 500 ml of MC, a MC layer was extracted using a separatory funnel. After adding Na$_2$SO$_4$ thereto to remove water, the resultant was concentrated. 46.4 g of Compound 1b was obtained (yield: 95%).

3. Synthesis of H-Lys-Lys-OH (Compound 1c)

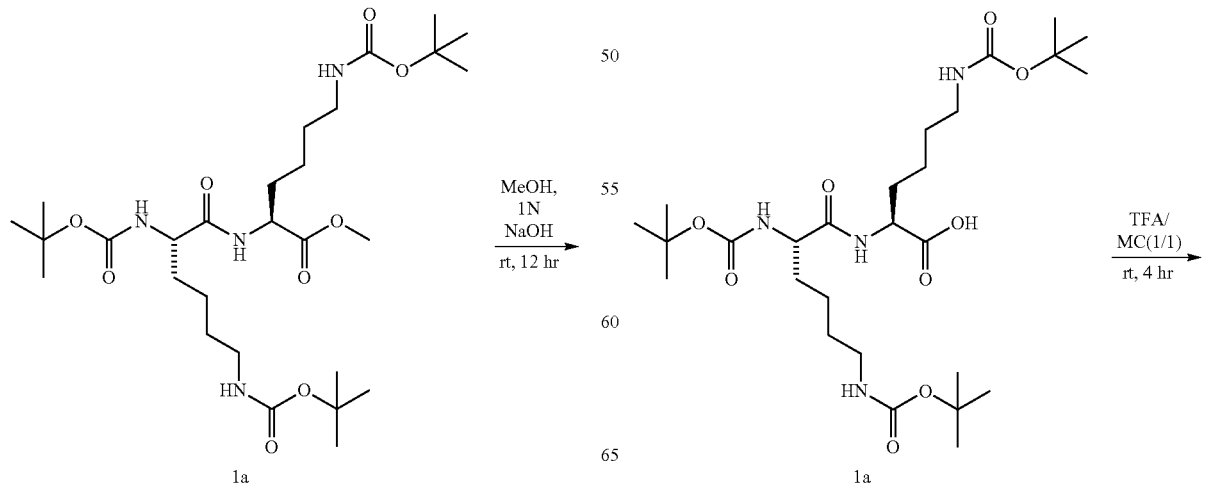

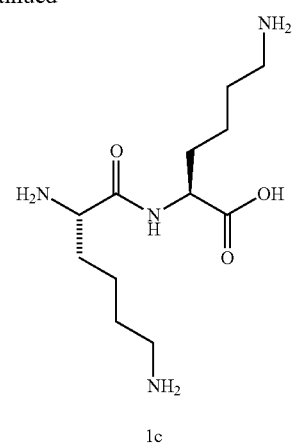

1c 40 g of Compound 1B (69.64 mmol, 1 equivalent) was put into a 2 L round flask, and dissolved in 200 ml of MC. 200 ml of trifluoroacetic acid (TFA) was added thereto, and a reaction was carried out at room temperature for 4 hours. After MC was removed using a concentrator, 500 ml of diethyl ether was added thereto to precipitate a product. A solid product was collected by filtering, and the collected solid product was washed with 300 ml of diethyl ether. After dissolving the obtained solid product in 300 ml of water, followed by freeze drying, thereby obtaining 31.5 g of Compound 1c in a TFA salt form.

Example 1-2. Alkylation Reaction

1. Synthesis of (tert-butoxycarbonylmethyl)$_2$-Lys(tert-butoxycarbonylmethyl)$_2$-Lys(tert-butoxycarbonylmethyl)$_2$-O(tert-butoxycarbonylmethyl) (Compound 1d)

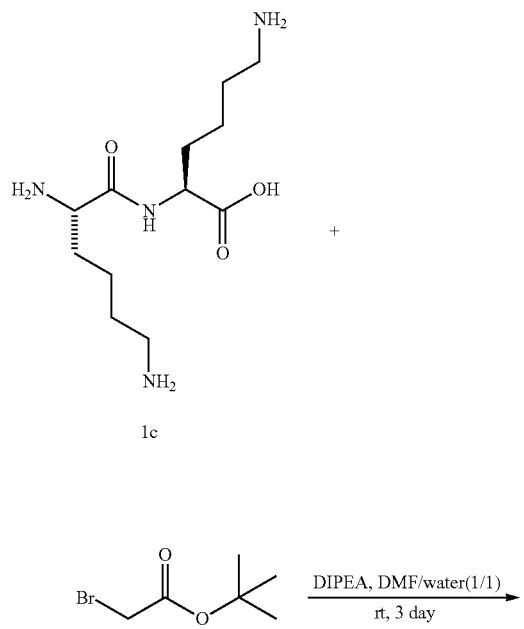

30 g of Compound 1c (59.74 mmol, 1 equivalent) was put into a 2 L round flask, and dissolved in 400 ml of water. 125 ml of N,N-diisopropylethylamine (DIPEA, 12 equivalents) was added thereto, and 400 ml of N,N-dimethylformamide (DMF) was added thereto. Finally, 61.3 ml of tert-butylbromoacetate (7 equivalents) was added thereto, and a reaction was carried out at room temperature for 3 days. The reaction was confirmed by thin layer chromatography (TLC, hexane:ethyl acetate=2:1, Rf=0.3). After adding 500 ml of EA, an EA layer was extracted using a separatory funnel. After 500 ml of an aqueous 1N HCl solution was added thereto, an EA layer was extracted using a separatory funnel (extraction was repeated six times). After 500 ml of an aqueous 5% NaHCO$_3$ solution was added thereto, an EA layer was extracted using a separatory funnel. After 20 ml of a saturated aqueous NaCl solution was added thereto, an EA layer was extracted using a separatory funnel. After adding Na$_2$SO$_4$ to remove water, the resultant was concentrated. 38.5 g of Compound 1d was obtained (yield: 60%).

Example 1-3. Hydrolysis Reaction

1. Synthesis of (tert-butoxycarbonylmethyl)$_2$-Lys(tert-butoxycarbonylmethyl)$_2$-Lys(tert-butoxycarbonylmethyl)$_2$-OH (Compound 1e)

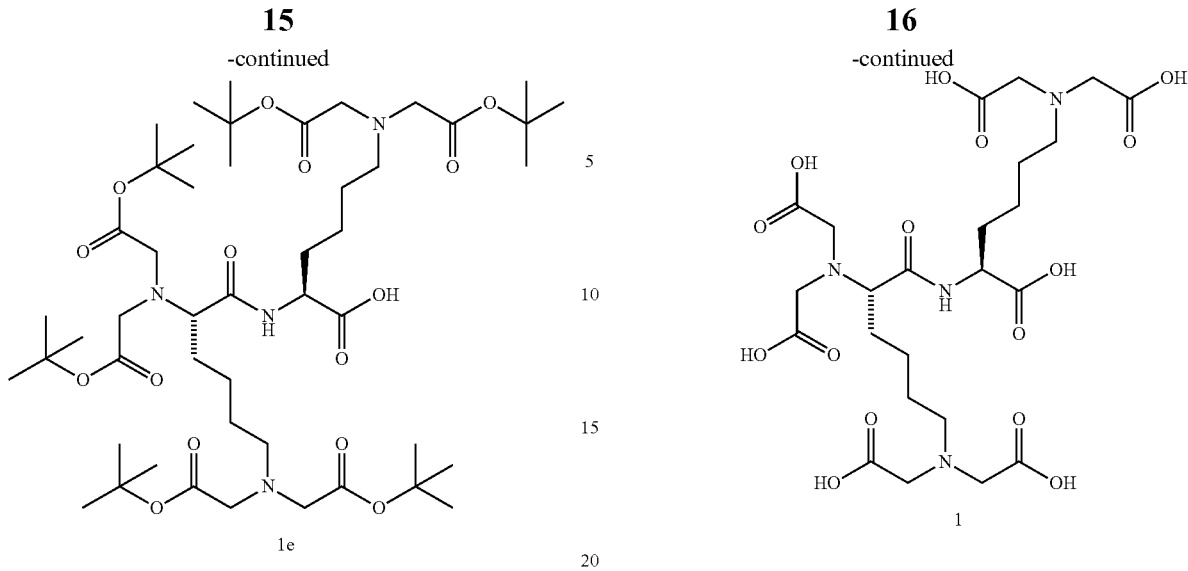

1e 30 g of Compound 1d (27.95 mmol, 1 equivalent) was put into a 2 L round flask, and dissolved by adding 600 ml of tetrahydrofuran (THF) thereto. After adding 216 ml of water thereto, 84 ml of an aqueous 1N NaOH solution (3 equivalents) was added thereto, and a reaction was carried out at room temperature for 12 hours. The reaction was confirmed by thin layer chromatography (TLC, MC:MeOH=10:1, Rf=0.4). THF was removed using a concentrator. After adding 500 ml of water thereto to dissolve the resultant, a pH of an aqueous solution was adjusted to 5 by adding sulfuric acid. After adding 500 ml of MC thereto, a MC layer was extracted using a separatory funnel. After adding $Na_2SO_4$ to remove water, the resultant was concentrated. 25.5 g of Compound 1e was obtained (yield: 95%).

Example 1-4. Protection Group Removal Reaction

1. Synthesis of Compound Represented by Structural Formula 1

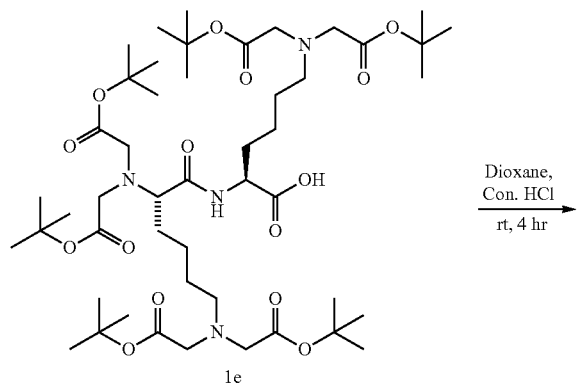

1e

Dioxane, Con. HCl
rt, 4 hr

1

Figure 2:
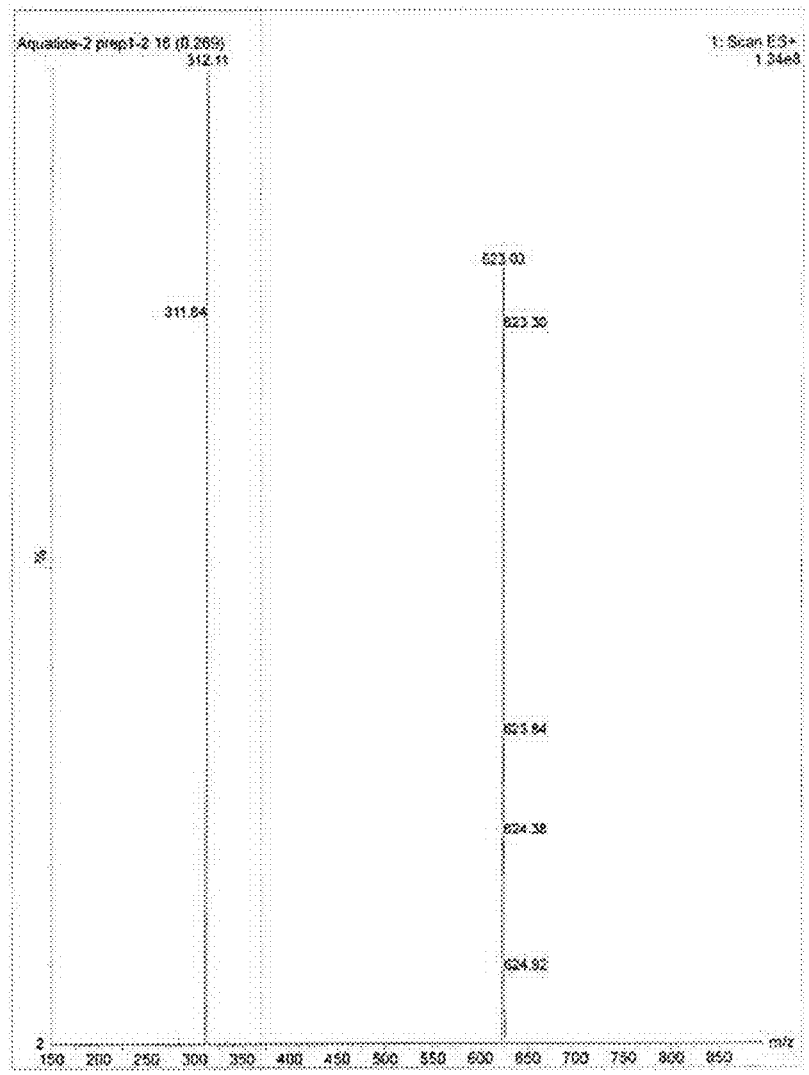
FIG. 2 illustrates a result obtained by performing liquid chromatography (LC)/mass spectrometry (MS) assay on the compound represented by Structural Formula 1.

20 g of Compound 1e (20.85 mmol, 1 equivalent) was put into a 1 L round flask, and dissolved by adding 200 ml of dioxane. 200 ml of an aqueous 35% HCl solution was added thereto, and a reaction was carried out at room temperature for 12 hours. The reaction was confirmed by HPLC (Shimadzu LC-20AD, GraceSmart RP C18 5u 120A 4.6*250 mm, Rt=3.668 min, 0.01% TFA containing acetonitrile (various concentration gradients: 0% to 20%)/water, 20 minutes) and LC/MS (Waters SQD2, MS(ESI)m/e, [M+H]+=623.03, [M+H]+/2=312.11). Water and dioxane were removed using a concentrator. After adding 300 ml of water thereto to dissolve the resultant, the resultant was concentrated again (this process was repeated four times). After adding 300 ml of water to dissolve the resultant, the resultant was freeze-dried. 12.3 g of the compound represented by Structural formula 1 was obtained (yield: 95%). HPLC assay (FIG. 1) and LC/MS assay (FIG. 2) were performed on the obtained compound represented by Structural Formula 1.

Example 2. Measurement of In-Vitro Anti-Oxidant Activity by Compound Represented by Structural Formula 1

In order to measure in-vitro anti-oxidant activity of the compound represented by Structural Formula according to the present invention, ABTS radical scavenging assay was performed. When 2,2'-azino-bis-(3-ethylbenzothiazoline-6-sulfonic acid (ABTS) reacts with potassium persulfate, $ABTS^+$, which is an active cation, is formed, but in the case in which an anti-oxidant material is present in a test sample, $ABTS^+$ is removed by anti-oxidant activity, a greenish blue color, which is a peculiar color of $ABTS^+$, is decolorized, which may be measured as an absorbance value, thereby making it possible to evaluate the anti-oxidant activity.

As a specific experimental method, after mixing ABTS diammonium salt (7 mM) and potassium persulfate (2.45 mM) with each other in distilled water in order to activate stabilized ABTS diammonium salt, a reaction was carried out at room temperature for 16 hours, thereby forming an ABTS radical. After diluting the resultant in a phosphate buffer solution (PBS) to prepare a reaction solution so that an OD734 value was about 1.5, the reaction solution was mixed with vitamin C (Vit C), pyrrolidone carboxylic acid (PCA), or the compound represented by Structural Formula 1 disclosed in the present invention to induce a reaction. After 30 minutes, an amount of the remaining activated ABTS radical was analyzed by measuring absorbance at OD734.

Figure 3:
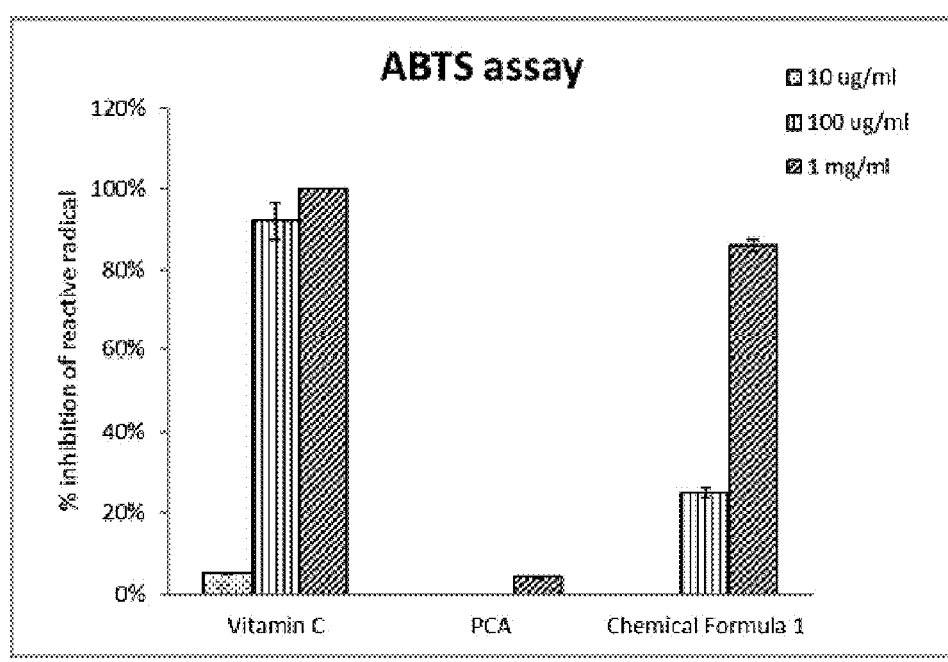
FIG. 3 illustrates a result obtained by confirming anti-oxidant activities of the compound represented by Structural Formula 1, vitamin C, and pyrrolidone carboxylic acid (PCA), respectively, using 2,2'-azino-bis-(3-ethylbenzothiazoline-6-sulfonic acid) (ABTS) radical scavenging assay.

As a result, vitamin C and the compound represented by Structural Formula 1 exhibited a concentration-dependent scavenging activity on the activated ABTS radical as illustrated in FIG. 3.

Example 3. Measurement of Intracellular Anti-Oxidant Activity by Compound Represented by Structural Formula 1

In order to measure an intercellular anti-oxidant activity of the compound represented by Structural Formula 1 according to the present invention, an amount of intracellular reactive oxygen species (ROS) was measured using 6-carboxy-2',7'-dichlorofluorescein diacetate (DCFH-DA) dye and fluorescence activated cell sorter (FACS) scanning. When DCFH-DA is introduced into cells through a cell membrane, DCFH-DA is hydrolyzed to 6-carboxy-2',7'-dichlorofluorescein (DCFH) by esterase existing in a cytoplasm, and when there is an intracellular ROS, DCFH is oxidized to fluorescent dichlorofluorescein (DCF), thereby exhibiting green fluorescence with a high fluorescence intensity (excitation at 485 nm, emission at 515 nm). Therefore, since in the case of pre-treating cells with a test material, inducing oxidative stress using hydrogen peroxide ($H_2O_2$), or the like, and treating the cells with DCFH-DA, a fluorescence intensity of DCF is differently exhibited depending on a degree of an anti-oxidative capacity of the test material, an intracellular anti-oxidant activity of the test material may be measured using the fluorescence intensity as described above.

As a specific experimental method, human epidermal keratinocyte cells (Gibco BRL) were uniformly seeded onto a 600 culture dish ($3 \times 10^5$ cells/dish) and cultured in an epilife medium (Gibco BRL) containing human keratinocyte growth supplement (HKGS, Gibco BRL) at 37° C. in a 5% $CO_2$ incubator for 24 hours. Thereafter, the test materials ($H_2O_2$, vitamin C, and the compound represented by Structural Formula 1) were each dissolved in water at a concentration of 10 mM to prepare a concentrate, the prepared concentrate was diluted so as to have a concentration of 100 uM using the medium and put into a culture dish to treat the cells. Then, culturing was performed for 48 hours, and after the culturing was terminated, the medium was removed and the resultant was washed, thereby preparing a subsequent experiment. Next, 10 uM hydrogen peroxide was added thereto, the culturing was performed for 10 minutes, the resultant was washed again. After 10 uM DCFH-DA was added thereto again, and additional culturing was performed for 60 minutes, entire cells were obtained by treating the resultant with trypsin. Thereafter, florescence intensities of individual cells were confirmed (excitation at 485 nm, emission at 515 nm) using FACS caliber (Becton Dickinson).

Figure 4:
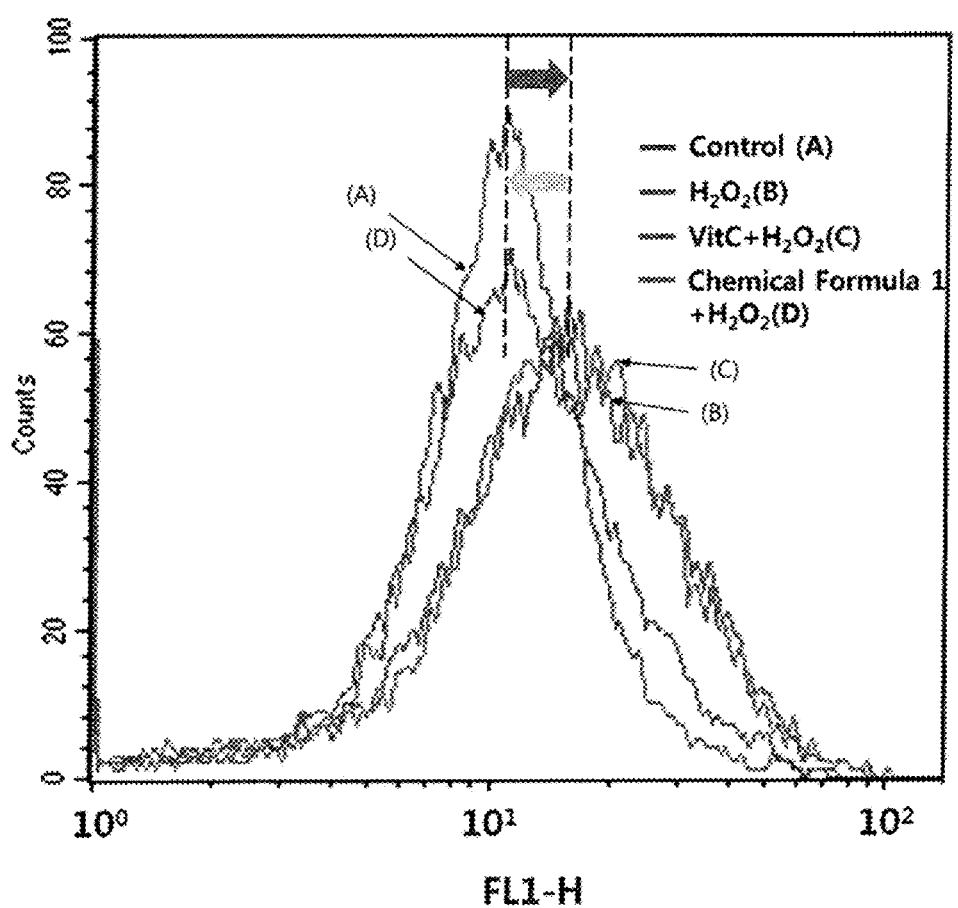
FIG. 4 illustrates a result obtained by confirming an intracellular anti-oxidant activity of the compound represented by Structural Formula 1 inhibiting formation of intracellular reactive oxygen species (ROS) using 6-carboxy-2',7'-dichlorofluorescein diacetate (DCFH-DA) dye assay and fluorescence activated cell sorter (FACS) scanning. A horizontal axis means a fluorescence intensity detected in each cell, and a vertical axis means a cell count. A (A) line indicates a non-treated control group, a (B) line indicates a group treated with $H_2O_2$, a (C) line indicates a group treated with $H_2O_2$ and vitamin C, and a (D) line indicates a group treated with $H_2O_2$ and the compound represented by Structural Formula 1. The (B) line indicates the group treated only with $H_2O_2$, and a right shift from the (A) line (the non-treated group) to the (C) line means a state in which the intracellular ROS was formed, and a left shift to the (D) line by treatment of the compound means that the intracellular ROS was decreased.

As a result, it may be confirmed that in the case of pre-treatment with vitamin C for 48 hours, an amount of intracellular ROS formed by treatment with treatment of $H_2O_2$ was not decreased, but in the case of pre-treatment with the compound represented by Structural Formula 1 for 48 hours, intracellular ROS formed by treatment with $H_2O_2$ almost disappeared as illustrated in FIG. 4.

Example 4. Measurement of Expression Amounts of Anti-Oxidant Protein and Autophagy-Related Protein by Compound Represented by Structural Formula 1

In order to find a cause of increasing an intracellular anti-oxidant activity by treatment with the compound represented by Structural Formula 1, cDNA microarray was performed, thereby confirming that transcription of several kinds of important genes associated with anti-oxidation and autophagy was increased. Proteins for the selected genes were quantified by western blot.

As a specific experimental method, after treating human epidermal keratinocyte cells (Gibco BRL) with the compound represented by Structural Formula 1 at a concentration of 50, 100, or 200 um while culturing the cells in a 600 culture dish, culturing was performed for 48 hours. After the culturing was terminated, a medium was removed, a RIPA lysis buffer containing protease inhibitor cocktail (2 ug/ml aprotinin, 5 ug/ml leupeptin, 1 ug/ml pepstatin A, 1 mM PMSF, 5 mM EDTA and 1 mM EGTA) was added thereto, thereby obtaining an entire cell homogenate. Thereafter, total proteins were quantified through microBCA assay (SMART micro BCA protein assay kit, Intron biotechnology), the cell homogenate (10 to 20 ug) was loaded on a SDS-PAGE gel, and respective proteins were isolated by electrophoresis and moved to a nitrocellulose membrane. Then, non-specific binding was removed by a blocking buffer, and after reacting antibodies (anti-Prx2, anti-Prx3, anti-Grp75, anti-HSP90B1, anti-EPHX2, anti-Stanniocalcin2, anti-Bip, anti-Foxo1, anti-Sirt5 and anti-n actin) for the respective proteins and HRP-bound secondary antibodies (anti-rabbit IgG HRP(sigma), anti-mouse IgG HRP(sigma)) thereof with each other, the reaction resultant was exposed to a photosensitive film by an enhanced chemiluminescence (ECL) method using a WestSave STAR ECL kit (Abfrontier), thereby confirming presence of the respective proteins and quantifying the respective proteins.

Figure 5:
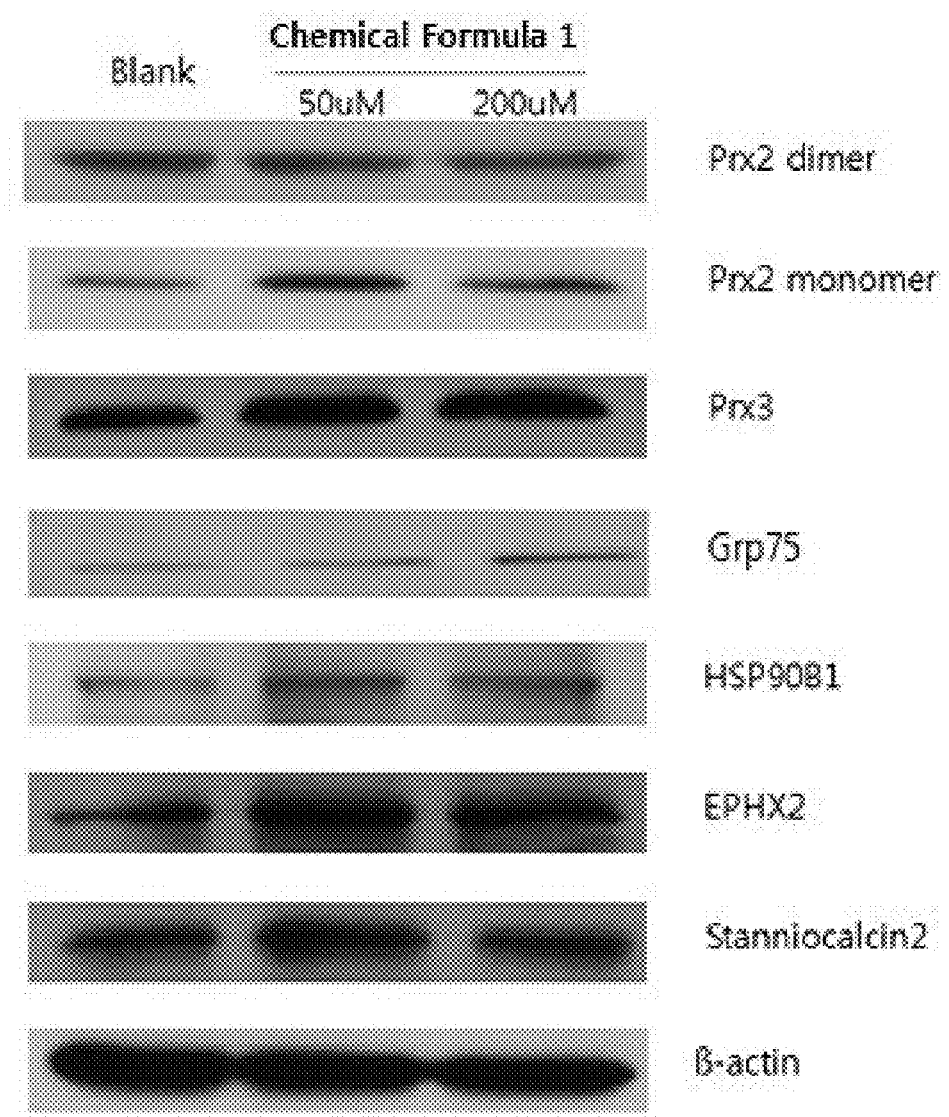
FIG. 5 illustrates a western block result obtained by measuring changes in expression amounts of aging-related proteins at the time of treating cells with the compound represented by Structural Formula 1.
Figure 6:
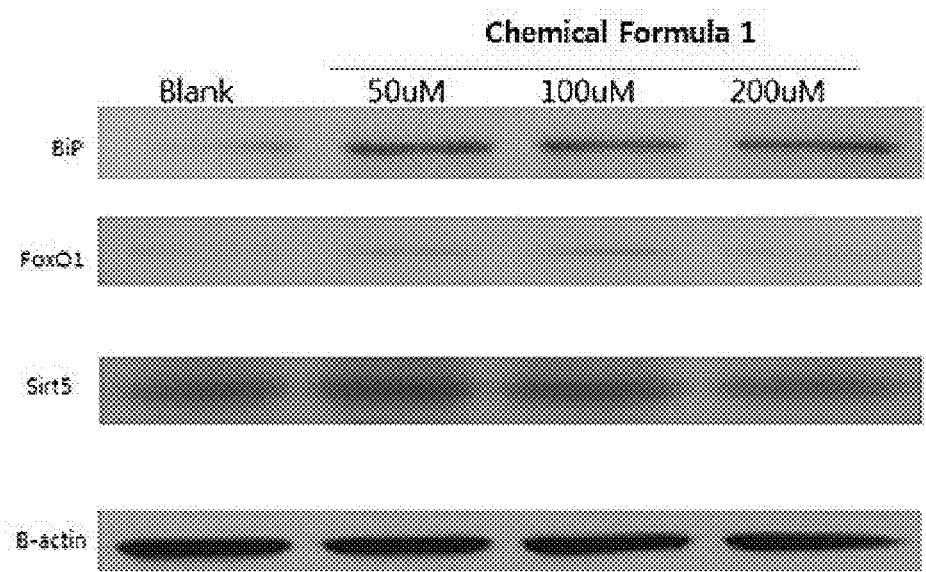
FIG. 6 illustrates a western block result obtained by measuring changes in expression amounts of autophagy-related proteins at the time of treating cells with the compound represented by Structural Formula 1.

As a result, it may be confirmed that at the time of treating the cells with the compound represented by Structural Formula 1, expression of proteins having high anti-oxidant activities such as a peroxiredoxin2 monomer (Prx2 monomer), peroxiredoxin3 (Prx3), HSP70 based Grp75, HSP90B1, epoxide dehydrogenase2 (EPHX2), stanniocalcin2, and the like, was increased as illustrated in FIG. 5. Further, it may be confirmed that expression of proteins important in autophagy and detoxification activities such as BiP, FoxO1, and sirtuin5 was increased as illustrated in FIG. 6.

Example 5. Measurement of Activation of Autophagy by Compound Represented by Structural Formula 1 Through LC3 Puncta Assay A possibility of activating autophagy in cells by treatment with the compound represented by Structural Formula 1 was confirmed through the result in Example 4, and in order to prove activation of autophagy, formation of light chain3 (LC3) puncta was confirmed.

As a specific experimental method, after 200 ul of poly-L-lysine (sigma) was put into each well of a 15 ul slide glass (Ibidi) and a reaction was carried out at room temperature for 30 minutes, followed by coating, human epidermal keratinocyte cells (Gibco BRL) were cultured and treated with respective test materials (rapamycin, compound represented by Structural Formula 1, and vitamin C) at a concentration of 100 uM. After the culturing for 48 hours was terminated, a medium was removed, and the cultured cells were fixed and blocked using formalin. Thereafter, the cells were labeled with anti-LC3 (Abfrontier) and anti-rabbit IgG-FITC (sigma), nucleus was stained with 4',6'-diamidine-2'-phenylindole dihydrochloride (DAPI), and then, whether or not a puncta was formed in the cells was confirmed using a confocal microscope.

Figure 7:
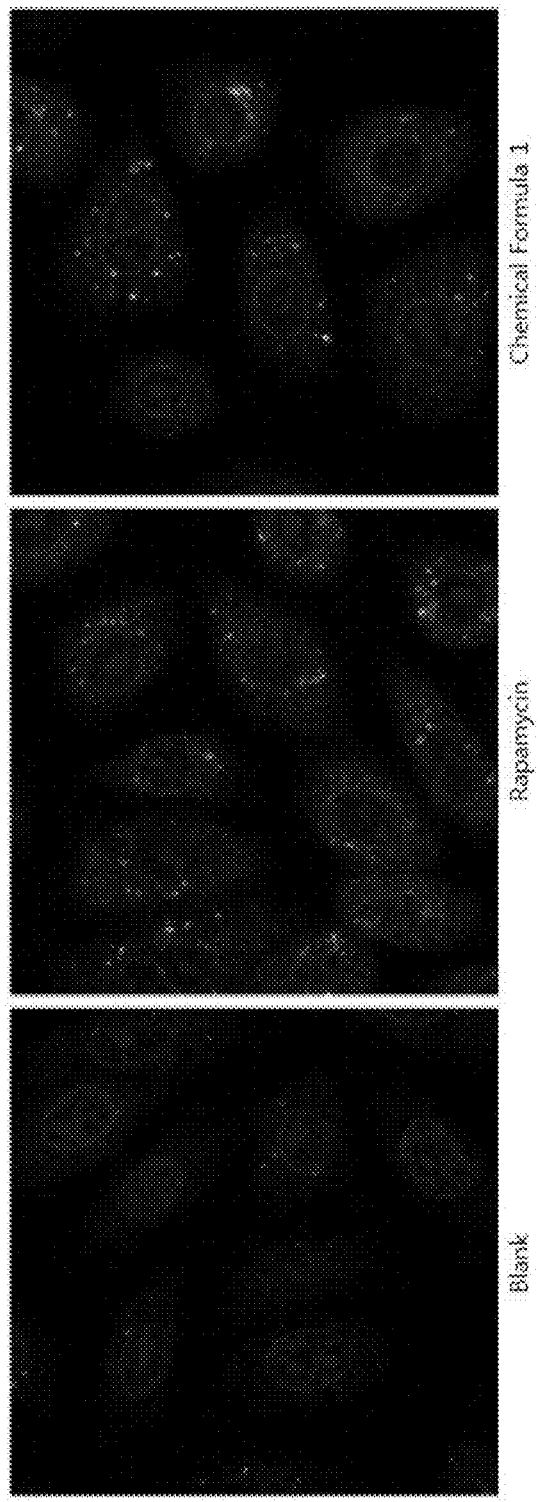
FIG. 7 illustrates a result obtained by confirming activation of autophagy by confirming whether or not LC3 puncta is formed in cases in which cells were treated with the compound represented by Structural Formula 1, rapamycin, or the cells were not treated.

As a result, it may be confirmed that similarly to rapamycin known as a material inducing autophagy, at the time of treating the cells with the compound represented by Structural Formula 1, a large amount of a LC puncta (a spot considered as a autophagosome) was formed in the cells as illustrated in FIG. 7. On the contrary, formation of the LC3 puncta was not increased by treatment with vitamin C.

The light chain 3 (LC3) is a protein similar to ubiquitin, and LC3-I and phosphatydilethanolamine (PE) are bound to each other to form LC3-II. LC3-II is inserted into a membrane of the autophagosome to form a structure of the autophagosome. When the autophagosome is formed, insertion of LC3-II into the membrane of the autophagosome is an important step which consistently occurs, and an amount of LC3 reflects a relative amount of the autophagosome in cells. When the LC3-II protein is bound to the autophagosome, the LC3-II protein seems to be a puncta like a vesicle at the time of observation using a cell immunostaining method.

Therefore, the large amount of LC puncta was formed by treatment with the compound represented by Structural Formula 1 according to the present invention, which is an important basis for the fact that the compound activates autophagy in cells.

Example 6. Measurement of Activation of Autophagy by Compound Represented by Structural Formula 1 Through Electron Microscopy Assay The activation of autophagy in cells by treatment with the compound represented by Structural Formula 1 was confirmed by the result in Example 5, and in order to more clearly prove this result, a structure in a cell was analyzed by an electron microscope.

As a specific experimental method, after treating human dermal fibroblast cells with the compound represented by Structural Formula 1 at a concentration of 50 uM while culturing the cells, the culturing was performed for 24 hours. After the culturing was terminated, the cells were fixed, a paraffin block was prepared, and then, cell images were analyzed using an electron microscope.

Figure 8:
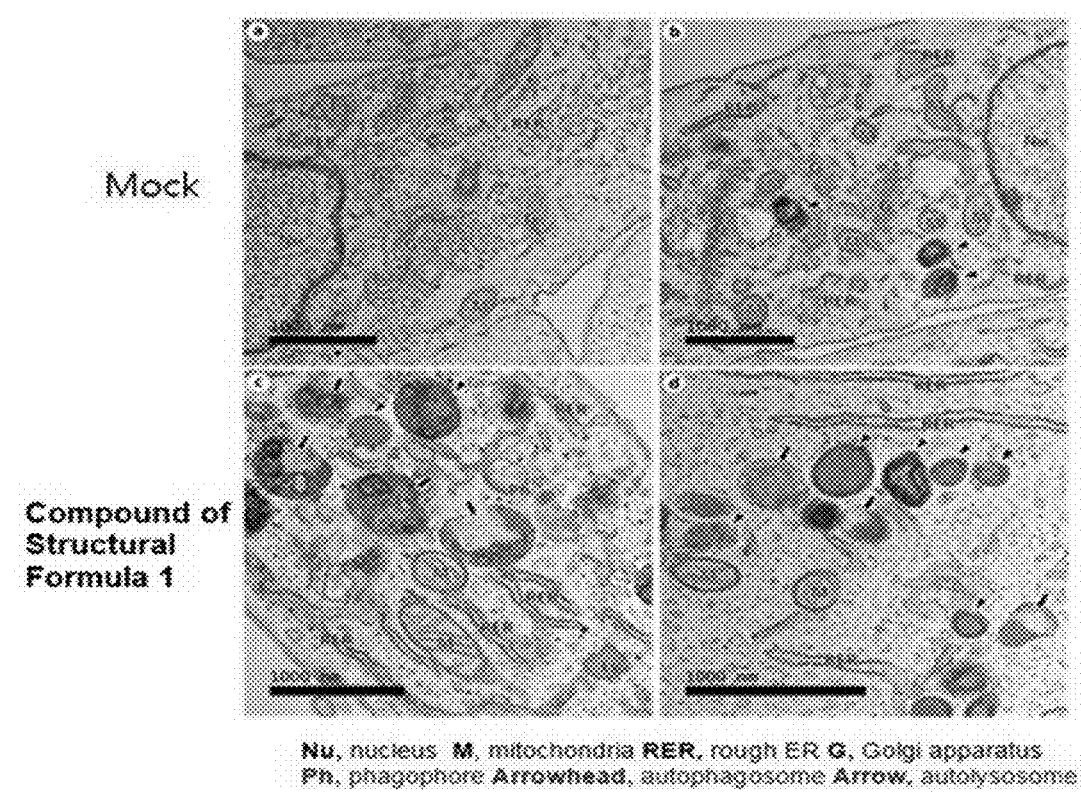
FIG. 8 are photographs obtained by analyzing cell images through an electron microscope after treating human dermal fibroblast cells with the compound represented by Structural Formula 1 and culturing the human dermal fibroblast cells for 24 hours.
Figure 9:
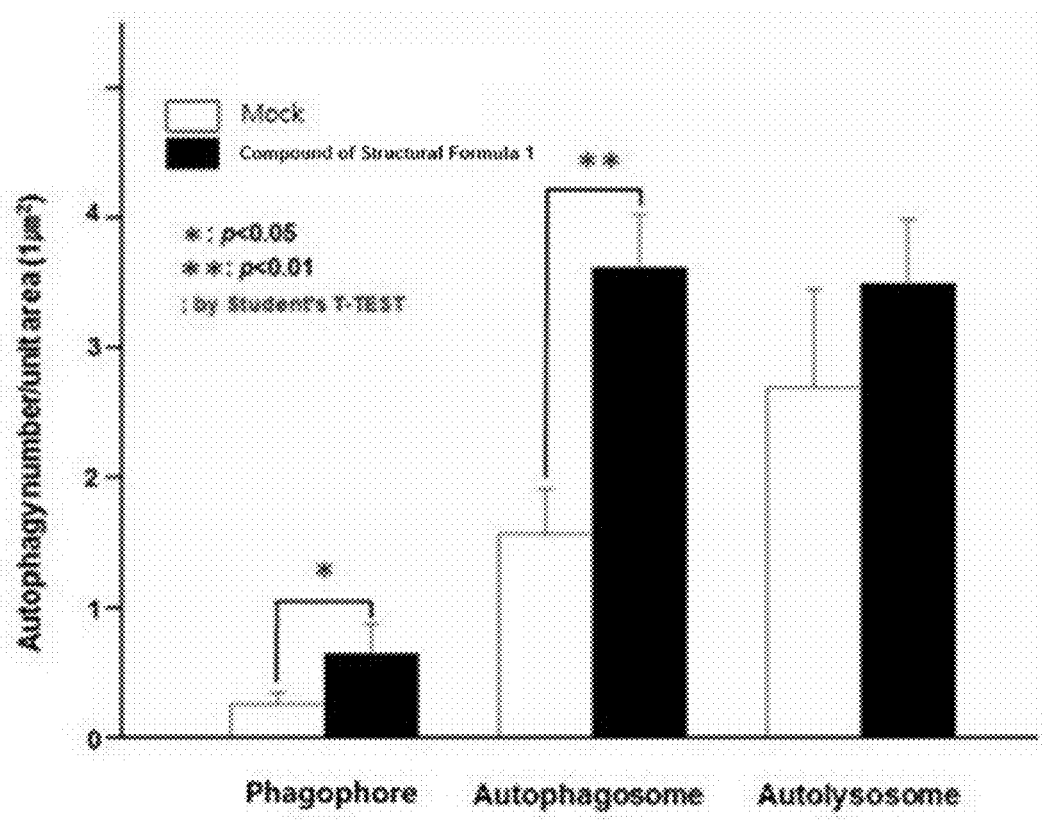
FIG. 9 illustrates a result obtained by quantitatively analyzing the numbers of intracellular phagophore, autophagosome, and autolysosome in an electron microscope photograph.

As a result, it was confirmed that at the time of treating the cells with the compound represented by Structural Formula 1, large amounts of phagophore, autophagosome, and autophagolysosome were formed as illustrated in FIGS. 8 and 9. As a result of measuring the numbers of phagophore, autophagosome, and autophagolysosome in cells in a large number of electron microscope photographs for quantitative analysis, it was observed that the number of autophagosome was significantly increased about 2 times or more by treatment with the compound represented by Structural Formula 1, and the numbers of phagophore and autophagolysosome were also significantly increased.

An autophagy pathway starts from formation of an isolated precursor membrane having a cup shape, referred to as phagophore. The phagophore may form a double membrane endoplasmic reticulum known as autophagosome through initiation, nucleation, elongation, and closure processes. The autophagosome carries condensed proteins, organelles or pathogenic bacteria in damaged cells to lysosome in a captured state, and fused with lysosome to form autophagolysosome. The autophagolysosome decomposes the captured constituents in an acidic environment mediated by acid hydrolase.

Therefore, phagophore, autophagosome, and autophagolysosome were significantly increased by treatment with the compound represented by Structural Formula 1 in the present Example, which is an important basis for the fact that the compound activates autophagy in cells.

Example 7. Measurement of Cell Protection Effect by Compound Represented by Structural Formula 1

Through the results in Examples 2 to 6, it was confirmed that expression of the anti-oxidant proteins and the autophagy-related proteins in cells was increased by the compound represented by Structural Formula 1, and thus, autophagy in the cells was activated. Therefore, in order to confirm whether or not activation of autophagy as described above may protect cells from cytotoxicity caused by ROS, follow-up research into a cell protection effect was conducted.

As a specific experiment method, after treating human epidermal keratinocyte cells (Gibco BRL) with respective test materials (vitamin C and the compound represented by Structural Formula 1) at 0.1 mM or 1 mM, respectively, while culturing the cells in a 96-well culture dish, the cells were cultured for 24 hours or 48 hours, the resultant was washed, and 1 mM $H_2O_2$ was added thereto, and additional culturing was performed for 4 hours. Thereafter, each of the wells was washed, 10 ul of 3-(4,5-dimethylthiazol-2-yl)-2,5-diphenyltetrazolium bromide (MTT) dissolved in PBS (5 mg/ml) was added to each of the wells, and a reaction was carried out at 37° C. under a 5% $CO_2$ condition. Thereafter, a supernatant was carefully removed, MTT formazan precipitated in the cells was dissolved in 100 ul of DMSO, and then absorbance at OD570 was measured using an enzyme-linked immunosorbent assay (ELISA) reader.

Figure 10:
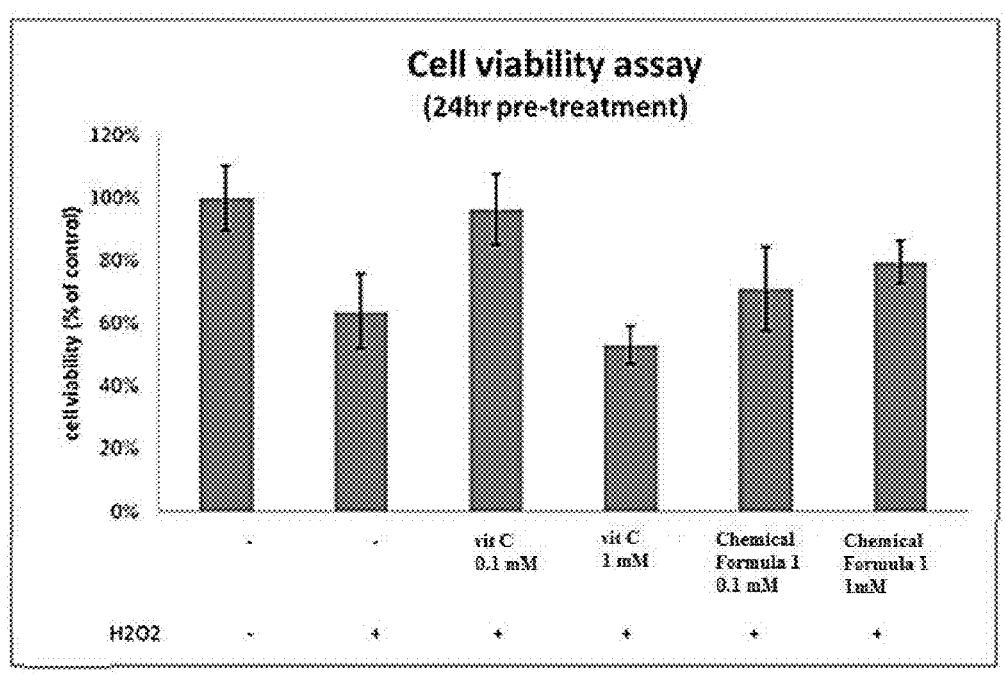
FIG. 10 illustrates cell viability (%) at the time of inducing oxidative stress using $H_2O_2$ after pre-treating cells with the compound represented by Structural Formula 1 or vitamin C for 24 hours.
Figure 11:
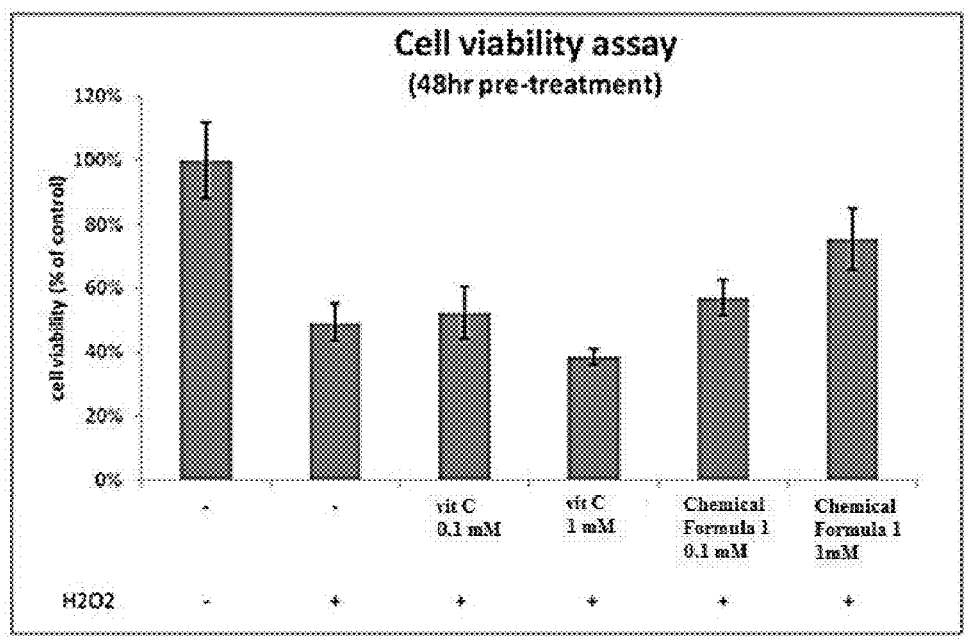
FIG. 11 illustrates cell viability (%) at the time of inducing oxidative stress using $H_2O_2$ after pre-treating cells with the compound represented by Structural Formula 1 or vitamin C for 48 hours.

As a result, it may be confirmed that in the case of vitamin C known as an anti-oxidant, at a concentration of 0.1 mM, at the time of pre-treatment for 24 hours recovered cell viability closely to 95%, and at the time of pre-treatment for 48 hours, recovery of cell viability was hardly observed, and at a concentration of 1 mM, at the time of pre-treatment for 24 hours or 48 hours, cell viability was rather deteriorated as illustrated in FIGS. 10 and 11. On the contrary, it may be confirmed that in the case of the compound represented by Structural Formula 1, at the time of pre-treatment for 24 hours or 48 hours, cell viability was improved.

The formulation containing the compound according to the present invention may activate autophagy, protect cells from oxidative stress, and protect cells, tissue, and an individual from various phenomena and diseases occurring due to the oxidative stress by increasing expression of the anti-oxidant proteins and autophagy-related proteins at the time of being applied to human-derived cells. Therefore, finally, the compound according to the present invention may be expected to treat or alleviate the aging phenomenon and diseases and suppress the aging phenomenon and diseases from being worsened, such that the compound may be evenly applied to formulations of various cosmetics, quasi-drugs, drugs, and food.

What is claimed is:

1. A cosmetic composition comprising a compound of the following Structural Formula 1 or a cosmetically acceptable salt thereof as an active ingredient:

Structural Formula 1

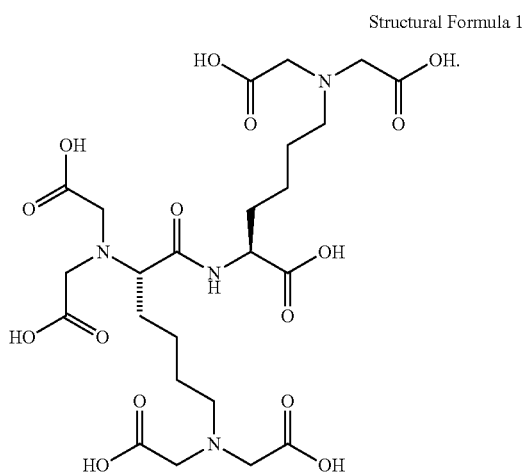 [SMILES: O=C(O)CN(CCCC[C@H](NC(=O)[C@H](CCCCN(CC(=O)O)CC(=O)O)N(CC(=O)O)CC(=O)O)C(=O)O)CC(=O)O]

2. A pharmaceutical composition comprising a compound of the following Structural Formula 1 or a pharmaceutically acceptable salt thereof as an active ingredient:

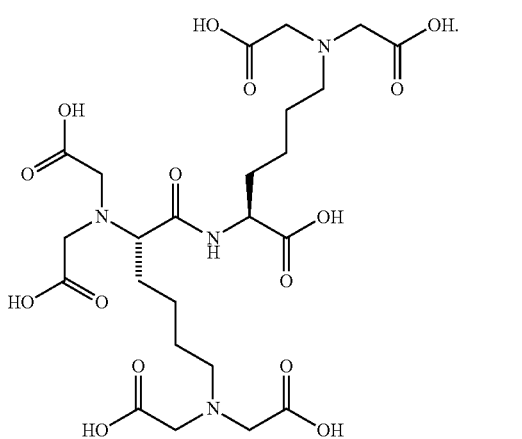

Structural Formula 1

3. The pharmaceutical composition according to claim 2, wherein the composition increases anti-oxidant and autophagy activities of cells.

4. A food composition comprising a compound of the following Structural Formula 1 or a cytologically acceptable salt thereof as an active ingredient:

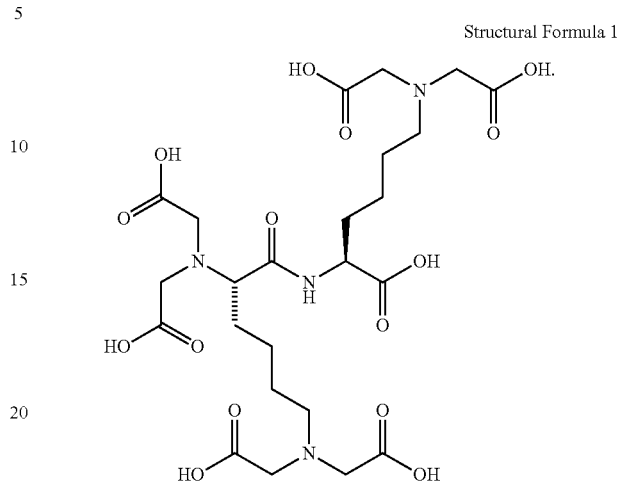

Structural Formula 1

5. The food composition according to claim 4, wherein the composition increases anti-oxidant and autophagy activities of cells.

* * * * *